United States Patent [19]

Wallach

[11] Patent Number: 5,019,392
[45] Date of Patent: * May 28, 1991

[54] ENCAPSULATION OF PARASITICIDES
[75] Inventor: Donald F. H. Wallach, Brookline, Mass.
[73] Assignee: Micro-Pak, Inc., Wilmington, Del.
[*] Notice: The portion of the term of this patent subsequent to Mar. 27, 2007 has been disclaimed.
[21] Appl. No.: 286,731
[22] Filed: Dec. 20, 1988

Related U.S. Application Data

[63] Continuation-in-part of Ser. No. 157,571, Mar. 3, 1988, Pat. No. 4,911,928, which is a continuation-in-part of Ser. No. 25,525, Mar. 13, 1987, abandoned, and a continuation-in-part of Ser. No. 78,658, Jul. 28, 1987, Pat. No. 4,855,090, and a continuation-in-part of Ser. No. 124,824, Nov. 24, 1987, Pat. No. 4,917,915.

[51] Int. Cl.$^5$ .................... A01N 25/26; A61K 9/127
[52] U.S. Cl. ............................. 424/420; 71/DIG. 1; 264/4.1; 424/450; 428/402.2; 514/963
[58] Field of Search .................... 264/4.1; 428/402.2; 424/420, 450; 514/963; 71/DIG. 1

[56] References Cited

U.S. PATENT DOCUMENTS

| | | | |
|---|---|---|---|
| 3,372,201 | 3/1968 | Leary et al. | 260/615 |
| 3,957,971 | 5/1976 | Oleniacz | 424/70 |
| 4,133,874 | 1/1979 | Miller et al. | 428/402.2 X |
| 4,150,141 | 4/1979 | Berger | 514/368 |
| 4,182,330 | 1/1980 | Michaels | 128/260 |
| 4,217,344 | 8/1980 | Vanlerberghe et al. | 424/450 |
| 4,235,871 | 11/1980 | Papahadjopoulos et al. | 424/ |
| 4,241,046 | 12/1980 | Papahadjopoulos et al. | 424/450 X |
| 4,247,411 | 1/1981 | Vanlerberghe et al. | 264/4.6 |
| 4,348,329 | 9/1982 | Chapman | 260/463 |
| 4,356,167 | 10/1982 | Kelly | 424/450 |
| 4,377,567 | 3/1983 | Geho | 424/1.1 |
| 4,485,054 | 11/1984 | Mezei et al. | 264/4.6 |
| 4,536,324 | 8/1985 | Fujiwara et al. | 252/311 |
| 4,544,545 | 10/1985 | Ryan et al. | 424/1.1 |
| 4,551,288 | 11/1985 | Kelly | 264/4.6 |
| 4,564,599 | 1/1986 | Janoff et al. | 436/507 |
| 4,588,578 | 5/1986 | Fountain et al. | 424/1.1 |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,666,711 | 5/1987 | Vanlerberghe et al. | 424/70 |
| 4,666,747 | 5/1987 | Quinn | 514/65 X |
| 4,684,625 | 8/1987 | Eppstein et al. | 514/19 |
| 4,692,433 | 9/1987 | Hostetler et al. | 514/12 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne et al. | 424/490 |
| 4,772,471 | 9/1988 | Vanlerberghe et al. | 424/450 |
| 4,911,928 | 3/1990 | Wallach | 424/420 X |

FOREIGN PATENT DOCUMENTS

| | | |
|---|---|---|
| 0032578 | 7/1984 | European Pat. Off. . |
| 0167825 | 6/1985 | European Pat. Off. . |
| 3410602 | 4/1984 | Fed. Rep. of Germany . |
| 59-106423 | 6/1984 | Japan . |
| 61-207324 | 9/1986 | Japan . |
| 85/01440 | 10/1984 | PCT Int'l Appl. . |
| 87/06499 | 11/1987 | PCT Int'l Appl. . |
| 929408 | 6/1963 | United Kingdom ................ 424/450 |
| 1539625 | 1/1979 | United Kingdom . |
| 2078543A | 1/1982 | United Kingdom . |
| 2079179A | 1/1982 | United Kingdom . |
| 2147263 | 9/1984 | United Kingdom . |
| 2198947 | 6/1988 | United Kingdom . |

OTHER PUBLICATIONS

*Diffusion of Univalent Ions Across the Lamellae of Swollen Phospholipids*, A. Bingham et al., J. Mol. Biol. 13, 238-252 (1965).
*McCutcheon's Detergents & Emulsifiers 1973 North American Edition*, p. 27.
*The Carrier Potential of Liposomes in Biology and Medicine* (First of Two Parts), G. Gregoriadis, The New England Journal of Medicine, 295, 704-710 (1976).
*Procedure for Prepration of Liposomes with Large Internal Aqueous Space and High Capture by Reverse-Phase Evaporation*, F. Szoka, Jr. et al., Proc. Natl. Acad. Sct. U.S.A. 75, 4194-4198 (1978).
*Methodes de Preparation des Liposomes*, N. Douseet et al., Puisieux and Delattre, Eds. Techniques et Documentation La Voisier Paris, pp. 41-42, (1985).
*McCutcheon's Emulsifiers & Detergents 1982 North American Edition*, pp 76-77.
*Liposomes*, edited by Marc J. Ostro, The Lipsome Co., Princeton, N.J., Marcel Dekker, Inc., New York and basel, pp. 246-249 (1983).
*A Very Mild Method Allowing the Encapsulation of Very High Amounts of Macromolecules into Very Large (1000 nm) Unilamellar Liposomes*, Philippot et al., Biochem, Biophys. Acta, 734, 137-143 (1983).
*Bilayer Fluidity of Non-Ionic Vesicles, An Investigation by Differential, Polarized Phase Fluorometry*, A. Ribier et al., Colloids and Surfaces 10, 155-161 (1984).
*The Preparation and Properties of Niosomes-Non-Ionic Surfactant Vesicles*, A. Baillie et al., J. Pharm. Pharmacol, 37, 863-88 (1985).
*Les niosomes*, R. Handjani-Vila et al., Les Lipsomes, Puisieux and Delattre, Eds. Techniques et Documentation La Voisier Paris, pp. 297-313.
*Extemporaneous Preparation of Large unilamellar Lipsomes*, J. Philippot et al., Biochem. Biophys. Acta, 821, 79-84 (1985).
*Problemes Technologiques Poses par l'utilisation des liposomes comme vecteurs de substances medicamenteuses, Encapsulation, sterilisation*, Conservation, F. Puisieux et al., Les Liposomes, Eds. Techniques et Documentation La Voisier Paris pp. 73-113 (1985).
*Non-ionic Surfactant Vesicles, Niosomes, as a Delivery System for the Anti-Leishmanial Drug, Sodium Stibogluconate*, A. Baillie et al., J. Pharm. Pharmacol, 38, 502-505, (1986).

Primary Examiner—Richard D. Lovering
Attorney, Agent, or Firm—Lahive & Cockfield

[57] ABSTRACT

The present invention relates to encapsulated parasiticides, a method for their production, and methods of treatment to prevent or eradicate infestation using the encapsulated parasiticides. The formulations of the present invention are water or oil-based and have many advantages over conventional formulations in safety, cost, and utility.

18 Claims, No Drawings

ENCAPSULATION OF PARASITICIDES

REFERENCE TO RELATED APPLICATIONS

This application is a continuation-in-part of U.S. patent application Ser. No. 157,571, filed Mar. 3, 1988, and now U.S. Pat. No. 4,911,928 entitled "Paucilamellar Lipid Vesicles," which is a continuation-in-part of U.S. patent application Ser. No. 025,525, (now abandoned) filed Mar. 13, 1987, entitled "Method of Producing High Aqueous Volume Multilamellar Vesicles"; U. S. patent application Ser. No. 078,658, filed July 28, 1987, now U.S. Pat. No. 4,865,090, also entitled, "Method of Producing High Aqueous Volume Multilamellar Vesicles"; and U.S. patent application Ser. No. 124,824, filed Nov. 24, 1987, now U.S. Pat. No. 4,917,915 entitled "Lipid Vesicles Formed of Surfactants and Steroids." The present application is also related to U.S. patent application Ser. No 163,806, filed Mar. 3, 1988, now U.S. Pat. No. 4,895,452 entitled "Method and Apparatus for Producing Lipid Vesicles."

BACKGROUND OF THE INVENTION

The present invention relates to formulations for delivery of parasiticides. More particularly, disclosed are encapsulated parasiticides, a method of their production, and methods of treatment using these encapsulated parasiticides. The parasiticides are encapsulated within nonphospholipid lipid vesicles which are themselves dispersed or suspended in an oil or water-based medium.

The parasiticide formulations of the present invention are useful to prevent or eradicate infestation by a broad spectrum of pests, e.g., insects, acarines, and helminths. Most existing formulations of parasiticides use organic solvents in order to solubilize the parasiticides because they are generally insoluble in water. Using organic solvents for this purpose is problematic at best. The solvents are irritating to the skin, thereby requiring the user to wear bulky protective clothing. Organic solvents add significantly to the cost of the parasiticides so solubilized, and the parasiticides must then be stored in metal containers to prevent container breakdown. Further, despite these harsh conditions, many potentially advantageous parasiticides cannot be solubilized in high enough concentrations to render them suitable for use, and ordinarily cannot be used in combination with other parasiticides, which would increase efficacy and spectrum coverage, due to chemical incompatibility.

The formulations of the present invention can be either water or oil-based. The advantages of the present formulation over those using organic solvents are that the new formulations are less expensive, less hazardous, and less irritating. Storage is simpler in that the formulation may be packed in plastic rather than the previously obligatory metal containers. Further, using the formulations of the present invention will allow otherwise incompatible combinations of active ingredients, either in separate vesicles or having one encapsulated and one in solution, to be used.

Lipid vesicles have not been considered particularly good carriers for water-insoluble materials such as parasiticides because of the instability of the lipid vesicles when carrying large quantities of lipophilic material. In addition, industrial use of lipid vesicles have been limited because of cost factors which are too high. Lipid vesicles are substantially spherical structures made of materials having a high lipid content, e.g., surfactants or phospholipids, organized in the form of lipid bilayers. The lipid bilayers encapsulate an aqueous volume which is either interspersed between multiple onion-like shells of lipid bilayers (forming multilamellar lipid vesicles or "MLV") and/or the aqueous volume is contained within an amorphous central cavity. The most commonly known lipid vesicles having an amorphous central cavity filled with aqueous medium are the unilamellar lipid vesicles. Large unilamellar vesicles ("LUV") generally have a diameter greater than about 1 $\mu$ while small unilamellar lipid vesicles ("SUV") generally have a diameter of less than 0.2 $\mu$. There are a variety of uses for lipid vesicles including the use as adjuvants or as carriers for a wide variety of materials.

Although substantially all the investigation of lipid vesicles in recent years has centered on multilamellar and the two types of unilamellar lipid vesicles, a fourth type of lipid vesicle, the paucilamellar lipid vesicle ("PLV"), exists. This lipid vesicle has barely been studied heretofore and until recently, has only been manufactured previously with phospholipids. PLV's consist of about 2 to 10 peripheral bilayers surrounding a large, unstructured central cavity. Normally, this central cavity was filled with an aqueous solution. See Callo and Mc Grath, Cryobiology 1985, 22(3), pp. 251-267.

Each type of lipid vesicle appears to have certain uses for which it is best adapted. For example, MLV's have a higher lipid content than any of the other lipid vesicles so to the extent that a lipid vesicle can carry a lipophilic material in the bilayers without degradation, MLV's have been deemed more advantageous than LUV's or SUV's for carrying lipophilic materials. In contrast, the amount of water encapsulated in the aqueous shells between the lipid bilayers of the MLV's is much smaller than the water which can be encapsulated in the central cavity of LUV's, so LUV's have been considered advantageous in transport of aqueous material. However, LUV's, because of their single lipid bilayer structure, are not as physically durable as MLV's and are more subject to enzymatic degradation. SUV's have neither the lipid or aqueous volumes of the MLV's or LUV's but because of their small size have easiest access to cells in tissues.

PLV's, which can be considered a sub-class of the MLV's, are a hybrid having features of both MLV's and LUV's. PLV's appear to have advantages as transport vehicles for many uses as compared with the other types of lipid vesicles. In particular, because of the large unstructured central cavity, PLV's are easily adaptable for transport of large quantities of aqueous-based materials. Also as illustrated in previously cited U.S. patent application Ser. No. 157,571, filed Mar. 3, 1988 and now U.S Pat. No. 4,911,928, the aqueous cavity of the PLV's can be filled wholly or in part with an apolar oil or wax which acts as a vehicle for the transport or storage of hydrophobic materials. The amount of hydrophobic material which can be transported by the PLV's with an apolar core is much greater than can be transported by MLV's. The multiple lipid bilayers of the PLV's provides PLV's with additional capacity to transport lipophilic material in their bilayers as well as with additional physical strength and resistance to degradation as compared with the single lipid bilayer of the LUV's.

All of the early lipid vesicle or liposome studies used phospholipids as the lipid source for the bilayers. The reason for this choice was that phospholipids are the principal structural components of natural membranes.

However, there are many problems using phospholipids as artificial membranes. Isolated phospholipids are subject to degradation by a large variety of enzymes. The most easily available phospholipids are those from natural sources, e.g., egg yolk lecithin, which contain polyunsaturated acyl chains that are subject to autocatalytic peroxidation. When peroxidation occurs, the lipid structure breaks down, causing premature release of encapsulated materials and the formation of toxic peroxidation byproducts. This problem can be avoided by hydrogenation but hydrogenation is an expensive process, thereby raising the cost of the starting materials. A kilogram of egg yolk lecithin pure enough for pharmacological liposome production presently costs in excess of $1,000. This is much to high a cost for a starting material for most applications. Even less highly purified phospholipids are too expensive for most animal uses.

Recently, there has been some indication, particularly from L'Oreal and Micro Vesicular Systems, Inc., that commercially available surfactants might be used to form the lipid bilayer in liposome-like multilamellar lipid vesicles. Both surfactants and phospholipids are amphiphiles, having at least One lipophilic acyl or alkyl group attached to a hydrophilic head group. The head groups are attached to one or more lipophilic chains by ester or ether linkages. Commercially available surfactants include the Brij family of polyoxyethylene acyl ethers, the SPAN sorbitan alkyl esters, and the TWEEN polyoxyethylene sorbitan fatty acid esters, all available from ICI Americas, Inc. of Wilmington, Delaware.

The methods and materials disclosed herein for producing the paucilamellar lipid vesicles all yield vesicles with a high aqueous or oil volume. Electron micrographs confirm that the paucilamellar lipid vesicles are distinct from the LUV's and the classic MLV's Accordingly, an object of the invention is to provide oil or water-based formulations for carrying parasiticides.

Another object of the invention is to provide formulations having parasiticides encapsulated within nonphospholipid vesicles A further object of the invention is to provide a method of preparing formulations of substantially water-insoluble parasiticides which exhibit antiparasitic action.

A still further object of the invention is to provide a method of treatment of plants, animals or their products to provide antiparasitic action.

These and other objects and features of the invention will be apparent from the following description.

SUMMARY OF THE INVENTION

The present invention features formulations having a parasiticide encapsulated in nonphospholipid lipid vesicles. The invention further features a method of preparing the vesicles and a method of treating plants, animals or products which provides antiparasitic action.

The formulation of the invention contains at least one active agent selected from a group consisting of insecticides, acaricides and anthelmintics, and mixtures, derivatives and analogs thereof, encapsulated in lipid vesicles. The lipid vesicles, which have nonphospholipid material as their primary lipid source, are dispersed in an aqueous-based carrier or may be dried and dispersed in an oil-based medium. As used herein, the term "disperse" means, includes and implies dispersions, suspensions, colloids, and other similar non-dissolved states.

Preferred nonphospholipid materials include lipid vesicle forming polyoxyethylene fatty esters, polyoxyethylene fatty acid ethers, diethanolamines, long-chain acyl amides, long-chain acyl amino acid amides, long-chain acyl amides, polyoxyethylene sorbitan oleates, polyoxyethylene glyceryl monostearates and monooleates, glycerol monostearates and monooleates, and mixtures, analogs, and derivatives thereof. The vesicles may also include a steroid and either a positive or negative charge producing agent. Preferred steroids include cholesterol, hydrocortisone, and their analogs, derivatives, and mixtures. Preferred negative charge producing materials are oleic acid, dicetyl phosphate, palmitic acid, cetyl sulphate, retinoic acid, phosphatidic acid, phosphatidyl serine, and mixtures thereof. In order to provide a net positive charge to the vesicles, long chain amines, e.g., stearyl amines or oleyl amines, long chain pyridinium compounds, e.g., cetyl pyridinium chloride, quaternary ammonium compounds, or mixtures of these can be used. A preferred positive charge producing material is hexadecyl trimethylammonium bromide, a potent disinfectant. The use of this disinfectant as the positive charge producing material within the vesicles provides a secondary advantage as the vesicles deteriorate; they act as a sustained release germicide carriers.

Although any type of lipid vesicle which could carry sufficient quantities of the parasiticides could be used, paucilamellar lipid vesicles are the most practical choice. These vesicles provide a large, amorphous central transport cavity which can be aqueous for water soluble compounds or apolar for non-aqueous soluble materials. That is, if the compound is not water soluble, the parasiticide can be dissolved or dispersed in a water immiscible oily material which can be used as a carrier, resulting in a non-aqueous core. As used herein, the term "water immiscible oily material" means, includes and implies oils and wax-like materials preferably selected from a group consisting of oils, waxes, natural and synthetic triglycerides, acyl esters, and petroleum derivatives, and their analogs and derivatives.

Water-insoluble ectoparasiticides are particularly suitable for inclusion in the present invention, and may include, but are not limited to, pyrethrins, pyrethroids, carbamates, water-insoluble organo-phosphorus compounds, benzoyl ureas, formamidines, triazines, avermectins, milbemycins, or other standard ectoparasiticides, and derivatives, analogs, and mixtures thereof. Cyhalothrin, cypermethrin, flumethrin, alphamethrin, deltamethrin, and permethrin are particularly preferred pyrethroids. Preferred carbamates are carbaryl and promacyl. A preferred formamidine is amitraz, and an effective triazine is cryomazine. Diazinon, pirimphos methyl, and pirimphos ethyl are especially effective water-insoluble organo-phosphorus compounds.

Water-insoluble endoparasiticides are equally suited for inclusion in the present invention and include the thiazoles and other standard anthelmintics, derivatives, analogs, and mixtures thereof. Preferred thiazoles include levamisole, dexamisole and tetramisole.

The formulation of the present invention may comprise one or more active ingredients. Both ingredients may be encapsulated in the same vesicle, or if the parasiticides are incompatible, separate vesicles may be used to encapsulate each and a dispersion made containing each type of vesicle. Alternatively, one active ingredient may be encapsulated in the vesicle, and the other dispersed in non-encapsulated form in a surrounding water or oil phase.

In one embodiment of the invention the parasiticide formulation is made by dispersing the parasiticide-containing vesicle in an aqueous-based solution and the parasiticide is encapsulated in a nonphospholipid lipid vesicle. The lipid vesicles are made by forming a lipophilic phase of a nonphospholipid material combined with any other lipophilic materials which are to be encapsulated, combining the water-insoluble parasiticides with a water immiscible oily material, disPersing the water immiscible oily material containing the parasiticide in the lipophilic phase, forming an aqueous phase of aqueous soluble materials to be encapsulated in the lipid vesicle by dispersing the aqueous soluble materials in an aqueous carrier, and shear mixing the lipophilic phase and the aqueous phase to form lipid vesicles. "Shear mixing" means, includes and implies the mixing of the lipophilic phase with the aqueous phase under turbulent or shear conditions which provide adequate mixing to hydrate the lipid and form lipid vesicles. Relative velocities of the phases are modified depending on the viscosity of the materials and the size of the orifices selected. "Shear mixing" is achieved by liquid shear which is substantially equivalent to a relative flow rate for the combined phases of about 5-30 m/s through a 1 mm radius orifice.

The lipid materials most useful in forming the vesicles of the invention can be classified as surfactants. However, standard methods of manufacture, although they may be used, are not as efficient as those set forth herein. In order to achieve the proper blending necessary to form paucilamellar lipid vesicles, all of the materials are normally in a flowable state. However, in the process of the present invention, use of a solvent for the lipid (the classic method of producing multilamellar lipid vesicles) is not only unnecessary; it is counter-productive. Many of the surfactants useful in the invention are liquids at room temperature or at slightly elevated temperatures so only gentle heating is necessary for flowability. Even the most difficult surfactants of the group to use, e.g., glycerol monostearate, can be easily handled at approximately 70° C. Therefore, one standard procedure of the invention is to elevate the temperature of the lipophilic phase in order to make it flowable followed by carrying out the shear mixing between the lipophilic phase and the aqueous phase at a temperature such that both phases are liquids. While it is often desirable to use the same temperature for both phases, this is not always necessary.

The formulation of the invention provides a method for control or eradication of infestation of pests. It may be used to treat animals, including humans, and may be used in human and veterinary medicine or public health control. The compounds of the invention have particular value in the control of those pests which are injurious to man or domestic animals, or which spread or act as vectors for diseases, for example, the control of ticks, mites, lice, fleas, midges, and biting, nuisance, or myiasis flies.

The formulation of the invention is also useful to protect plants, such as crops, or ornamental and forest trees, and it is also effective for protecting cut timber from attack by pests such as sawflies and beetles. Further, it may be applied to stored products such as grains and tobacco, and animal products such as hair, wool, feathers, and stored meat or fish to prevent attack by such pests as moths, beetles, mites, and flies.

Depending on the needs of the user, vesicle formulations may be applied by the pour-on method, or by conventional dip or spray technology. In addition, the vesicle formulation may be dried and dispersed in an oil medium suitable for use as a pour-on formulation for large animals, such as cattle.

DESCRIPTION OF THE INVENTION

The present invention solves a number of the problems encountered when using parasiticides because it allows aqueous formulations of water-insoluble parasiticides to be made. This avoids the problems stemming from the need for organic solvents or oils to solubilize the parasiticides, and allows greater flexibility in methods of administering the parasiticides. For example, the ability to add an endoparasiticide to drinking water yields a much easier method of treating animals than those presently used.

The preferred lipid vesicles are paucilamellar lipid vesicles having a water immiscible oily material within the amorphous central cavity. The water immiscible oily material can act as a carrier for the water-insoluble parasiticides.

Although any lipid vesicle forming material could, theoretically, be used to form the lipid vesicles of the invention, the most preferred surfactants useful in the invention are selected from a group consisting of polyoxyethylene fatty esters having the formula $$R_1-COO(C_2H_4O)_nH$$

where $R_1$ is lauric, myristic, cetyl, stearic, or oleic acid, or their derivatives and $n = 2-10$;

polyoxyethylene fatty acid ethers, having the formula $$R_2-CO(C_2H_4O)_mH$$

where $R_2$ is lauric, myristic, or cetyl acids or their derivatives, single or double unsaturated octadecyl acids or their derivative, or double unsaturated eicodienoic acids or their derivatives and m ranges from 2-4;

diethanolamines, having the formula $$(HOCH_2-CH_2)_2NCO-R_3$$

where $R_3$ is caprylic, lauric, myristic or linoleic acids or their derivatives;

long chain acyl hexosamides having the formula $$R_4-NOCO-(CH_2)_b-CH_3$$

where b ranges from 10—18 and $R_4$ is a sugar molecule selected from a group consisting of glucosamine, galactosamine, and N-methylglucamine;

long chain acyl amino acid amides having the formula $$R_5-CHCOOH-NOC-(CH_2)_c-CH_3$$

where c ranges from 10-18 and $R_5$ is an amino acid side chain;

long chain acyl amides having the formula $$HOOC-(CH_2)_d-N(CH_3)_2-(CH_2)_3-NCO-R_6$$

where $R_6$ is an acyl chain having 12-20 carbons and not more than two unsaturations, and d ranges from 1-3;

polyoxyethylene (20) sorbitan mono- or trioleate;

polyoxyethylene glyceryl monostearate or monooleate with 1-10 polyoxyethylene groups;

and glycerol monostearate or monooleate.

The paucilamellar lipid vesicles can be made by a variety of devices which provides sufficiently high shear for shear mixing. There are a large variety of these devices available on the market including a microfluidizer such as is made by Biotechnoloqy Development Corporation, a "French"-tyPe press, or some other device which provides a high enough shear force and the ability to handle heated, semiviscous lipids. If a very high shear device is used, it may be possible to microemulsify powdered lipids, under pressure, at a temperature below their normal melting points and still form the lipid vesicles of the present invention.

A device which is particularly useful for making the lipid vesicles of the present invention has been developed by Micro Vesicular Systems, Inc., Vineland, New Jersey and is further described in previously cited U.S. patent application Ser. No. 163,806, filed Mar. 3, 1988 and now U.S. Pat. No. 4,895,452. Briefly, this device has a substantially cylindrical mixing chamber with at least one tangentially located inlet orifice. One or more orifices lead to a reservoir for the lipophilic phase, mixed with an oil phase if lipid-core PLV's are to be formed, and at least one of the other orifices is attached to a reservoir for the aqueous phase. The different phases are driven into the cylindrical chamber through pumps, e.g., positive displacement pumps, and intersect in such a manner as to form a turbulent flow within the chamber. The paucilamellar lipid vesicles form rapidly, e.g., less than 1 second, and are removed from the chamber through an axially located discharge orifice. In a preferred embodiment, there are four tangentially located inlet orifices and the lipid and aqueous phases are drawn from reservoirs, through positive displacement Pumps, to alternating orifices. The fluid stream through the tangential orifices is guided in a spiral flow path from each inlet or injection orifice to the discharge orifice. The flow paths are controlled by the orientation or placement of the inlet or injection orifices so as to create a mixing zone by the intersection of the streams of liquid. The pump speeds, as well as the orifice and feed line diameters, are selected to achieve proper shear mixing for lipid vesicle formation. As noted, in most circumstances, turbulent flow is selected to provide adequate mixing.

The invention, and its uses, will be further explained by the following Examples.

EXAMPLE 1

Cyhalothrin is an ectoparasiticide of interest because of its effectiveness. It is oil-based and water-insoluble, and while effective, has proven difficult to solubilize in workable concentrations. To evaluate the versatility and effectiveness of the invention, a series of formulations were made by encapsulating cyhalothrin in lipid vesicles and suspending the cyhalothrin-filled vesicles in water to make the formulation of the invention. The vesicles are prepared by mixing cyhalothrin, a lipid vesicle-forming stock solution and water for a total proportion of 1/1/1 to produce a creamy suspension. The stock solution contains polyoxyethylene 2-cetyl ether (Brij 52 - ICI Americas, Inc.), cholesterol and palmitate in a ratio of 33/11/1.5. The lipid phase is first blended with the cyhalothrin at 60° C., then hydrated and the lipid vesicles are formed by shear mixing the lipid and aqueous phases with a device such as the Micro Vesicular Systems lipid vesicle forming machine previously described. Microscopy shows that the lipid vesicles formed consist of a yellow core of cyhalothrin with an optically diffused peripheral shell. All vesicles are distinct and there is no fusion between the vesicles. In fact, fusion cannot be induced by agitation, pressure, warming, or centrifugation. The vesicles resuspend easily in water at any dilution. The highest encapsulated concentration attempted is 33% cyhalothrin by volume and incorporation is essentially complete.

In another experiment following the same procedure, the Brij 52 (polyoxyethylene 2-cetyl ether) is replaced with POE 9 glyceryl monostearate. The same procedure was used for manufacture except a temperature of 70° C. is used to form the lipophilic phase. The resulting vesicles are substantially indistinguishable from the Brij 52 vesicles except this formulation holds up well at 52° C. while the former breaks down before reaching this temperature.

EXAMPLE 2

In this Example, a variation on the Brij 52 formulation of Example 1 was tested, replacing the parasiticide, cyhalothrin, with a 1:1 (v/v) ratio dispersion of the parasiticide in a water immiscible oily material, tristearin. The cyhalothrin and tristearin are blended at a temperature above the melting point of the mixture, 70° C., then blended with the Brij 52. All other ingredients, ratios, and conditions remain the same as in Example 1. This yields vesicles containing an encapsulation of cyhalothrin in tristearin.

External water may be removed by centrifugation and these liposomes can then be suspended in a variety of oils, such as corn oil, by addition of a small amount of a nonionic detergent. This approach yields a fine "pour-on" formulation which wets animal hair well enough to penetrate and flow along the skin surface.

EXAMPLE 3

To evaluate the relative effectiveness and utility of liposome formulations containing cyhalothrin, four different liposome preparations made by Micro Vesicular Systems, Inc., according to the formulations of Table 1, were tested. The biological efficiency of the cyhalothrin liposome products were evaluated and compared to that of a commercially available cyhalothrin product. The liposome products were designated L1--L4, and each contained 5% (w/v) cyhalothrin, as did the commercial emulsifiable concentrate (EC) formulation which was used as a positive control. The liposome preparations were diluted with an aqueous solution of surfactants identical to that used in the EC formulation to reduce variables within the test systems.

TABLE 1

| 5% Cyhalothrin Liposome Formulations | L1 | L2 | L3 | L4 |
|---|---|---|---|---|
| Brij 52 | 9.85 gm | 9.90 gm | 8.00 gm | 8.03 gm |
| Dicetyl Phosphate | 0.15 gm | none | 0.13 gm | none |
| Cetyl Trimethyl Ammonium Bromide | none | 0.10 gm | none | 0.09 gm |
| Cholesterol | none | none | 1.87 gm | 1.88 gm |
| Cyhalothrin | 5.00 gm | 5.00 gm | 5.00 gm | 5.00 gm |
| 10 mM Phosphate Buffer W/ 0.13M NaCl | 85.00 ml | 85.00 ml | 85.00 ml | 85.00 ml |

In one experiment, the adult tick immersion test was performed on the Malchi strain of B. microplus. This procedure tests the efficacy of the invention against a known commercial composition of cyhalothrin. Liposome preparations L1 and L2 were compared against the EC formulation over a range of concentrations by immersing groups of twenty fully engorged adult female ticks for ten minutes in 20 ml of an aqueous dilution of the test material. After drying, the ticks are retained in an incubator for fourteen days when assessments for inhibition of reproduction (IR) and kill (CL) are made.

A summary of the recorded data, presented in Table 2, shows effective cyhalothrin dose values for inhibition of reproduction (IR) and kill (LC) for each of the test materials. Regression analysis of the data using the GLIM statistical package showed that there is no significant difference in kill and IR between formulations.

TABLE 2

| Formulation | IR50 | IR95 | LC50 |
| --- | --- | --- | --- |
| EC | 27 ppm | 220 ppm | 390 ppm |
| Liposome L1 | 33 ppm | 170 ppm | 360 ppm |
| Liposome L2 | 28 ppm | 150 ppm | 350 ppm |

Other tests using the remaining formulations showed similar results.

EXAMPLE 4

In this Example, amitraz, an ectoparasiticide currently of interest which has widely divergent physical characteristics and activity from cyhalothrin, was encapsulated. The ability to encapsulate this parasiticide in the liposome formulations of the invention demonstrates the versatility and efficiency of the present lipid vesicle production process and the formulations produced. Use of amitraz as a parasiticide has proven problematical in the past as it is extremely difficult to solubilize by conventional means. However, the formulation of the invention permits encapsulation and use at concentrations higher than those previously possible.

Production of 5% amitraz liposomes can be accomplished according to the formulations in Table 3. The procedures are similar to those used in Example 2. It is not possible to encapsulate amitraz in aqueous solution at greater than 5% without depositing crystals and resulting in a high degeneration of the molecule. However, amitraz may be dissolved in triglycerides, e.g., tristearin, and suspended in an aqueous solution after encapsulation. Use of the melted triglycerides, such as tristearin or tripalmitin, as a carrier yields final amitraz concentrations of 5-10% (w/v). On prolonged storage at 4° C., preparations with 5% amitraz remain free of crystals, but crystals appear at 7.5%.

TABLE 3

| Formulas for 5% Amitraz Liposomes With 0.5% Staboxol | | | | |
| --- | --- | --- | --- | --- |
| Brij 52 | 9.85 gm | 9.90 gm | 8.37 gm | 8.40 gm |
| Dicetyl Phosphate | 0.15 gm | none | 0.15 gm | none |
| Cetyl Trimethyl Ammonium Bromide | none | 0.10 gm | none | 0.11 gm |
| Cholesterol | none | none | 1.48 gm | 1.49 gm |
| Staboxol | 0.50 gm | 0.50 gm | 0.50 gm | .50 gm |
| Amitraz | 5.00 gm | 5.00 gm | 5.00 gm | 5.00 gm |
| 10 mM Phosphate Buffer W/ 0.13M NaCl | 84.50 ml | 84.50 ml | 84.50 ml | 84.50 ml |

The foregoing Examples are expressly non-limiting and are merely to show the efficacy of the present invention. The invention is defined by the following claims.

What is claimed is:

1. A method of preparing a formulation exhibiting effective action against parasites, said formulation having a water insoluble parasiticide dispersed in a water immiscible oily material encapsulated in a paucilamellar lipid vesicle having an amorphous central transport cavity, said lipid vesicle having nonphospholipid materials as its primary lipid source, said method comprising the steps of:

a. Forming a lipophilic phase of said nonphospholipid materials combined with any other lipophilic materials to be encapsulated therein;

b. Combining said parasiticide with said water immiscible oily material;

c. Dispersing said water immiscible oily material containing said parasiticide in said lipophilic phase;

d. Forming an aqueous phase of any aqueous soluble materials to be encapsulated in said lipid vesicle, said aqueous materials being dispersed in an aqueous carrier; and e. Blending said lipophilic phase and said aqueous phase with shear mixing to form said paucilamellar lipid vesicles, whereby substantially all of said water immiscible oily material having said parasiticide dispersed therein is contained in said amorphous central transport cavity.

2. The method of claim 1 wherein said nonphospholipid material is selected from a group consisting of polyoxyethylene fatty esters, polyoxyethylene fatty acid ethers, diethanolamines, long chain acyl hexosamides, long chain acyl amino acid amides, long chain acyl amides, polyoxyethylene sorbitan oleates, polyoxyethylene glyceryl monostearates and monooleates, glycerol monostearates and monooleates, and mixtures thereof.

3. The method of claim 1 wherein said water insoluble parasiticide is an ectoparasiticide selected from a group consisting of pyrethrins, pyrethroids, carbamates, water-insoluble organo-phospphorus compounds, benzoyl ureas, formamidines, triazines, avermectins, milbemycins and mixtures thereof.

4. The method of claim 3 wherein said water insoluble ectoparasiticide is selected from a group consisting of cyhalothrin, amitraz, cypermethrin, flumethrin, alphamethrin, deltamethrin, permethrin, diazinon, pirimphos methyl, pirimphos ethyl and mixtures thereof.

5. The method of claim 1 wherein said water insoluble parasiticide is an endoparasiticide selected from a group consisting of thiazoles, other water insoluble endoparasiticides, and mixtures thereof.

6. The method of claim 5 wherein said water insoluble endoparasiticide is selected from a group further consisting of tetramisole, levamisole, dexamisole and mixtures thereof.

7. The method of claim 1 wherein said formulation further comprises at least two parasiticides.

8. A formulation active against parasites comprising at least one active water insoluble parasiticide dispersed in a water immiscible oily material which acts as a carrier, said water immiscible oily material encapsulated in the amorphous central transport cavity of a paucilamellar lipid vesicle, said lipid vesicle having a nonphospholipid material selected from the group consisting of polyoxyethylene fatty esters, polyoxyethylene fatty ethers, diethanolamines, long chain acyl hexosamides, long chain acyl amino acid amides, long chain acyl amides, polyoxyethylene sorbitan oleates, polyoxyethylene glyceryl monostearates and monooleates, glycerol monostearates and monooleates, and mixtures thereof as its primary lipid source.

9. The formulation of claim 8 wherein said lipid vesicle further comprises a steroid selected from the group consisting of cholesterol, hydrocortisone, and mixtures thereof.

10. The formulation of claim 8 wherein said lipid vesicle further comprises a charge-producing agent.

11. The formulation of claim 8 wherein said formulation comprises a plurality of parasiticides, each of said plurality being encapsulated in separate lipid vesicles.

12. The formulation of claim 8 wherein said parasiticide is active against parasites selected from a group consisting of insects, acarines, and helminths.

13. The formulation of claim 8 where said water insoluble parasiticide is an ectoparasiticide selected from a group consisting of pyrethrins, pyrethroids, carbamates, water-insoluble organo-phosphorus compounds, benzoyl ureas, formamidines, triazines, avermectins, milbemycins, and mixtures thereof.

14. The formulation of claim 8 wherein said water insoluble ectoparasiticide is selected from a group further consisting of cyhalothrin, amitraz, cypermethrin, flumethrin, alphamethrin, deltamethrin, permethrin, diazinon, pirimphos methyl, pirimphos ethyl and mixtures thereof.

15. The formulation of claim 8 wherein said water insoluble parasiticide is an endoparasiticide selected from a group consisting of thiazoles, other water insoluble endoparasiticides, and mixtures thereof.

16. The formulation of claim 15 wherein said water insoluble endoparasiticide is selected from a group further consisting of tetramisole, levamisole, dexamisole, and mixtures thereof.

17. A method of treatment of plants of their products to prevent or eradicate infestation with parasites comprising the step of treating with an effective amount of the formulation of claim 8.

18. A method of treatment of animals or their products to prevent or eradicate infestation with parasites comprising the step of treating with an effective amount of the formulation of claim 8.

* * * * *

UNITED STATES PATENT AND TRADEMARK OFFICE
CERTIFICATE OF CORRECTION

PATENT NO. : 5,019,392

DATED : May 28, 1990

INVENTOR(S) : Donald F.H. Wallach

It is certified that error appears in the above-identified patent and that said Letters Patent is hereby corrected as shown below:

Column 2, line 29, replace "then any" with --than any--.

Column 5, line 9, replace "disPersing" with --dispersing--.

Column 9, line 11, replace "kill (CL)" with --kill (LC)--.

Signed and Sealed this

Ninth Day of November, 1993

Attest:

BRUCE LEHMAN

*Attesting Officer*      *Commissioner of Patents and Trademarks*